United States Patent
Bhalay et al.

(10) Patent No.: US 7,754,758 B2
(45) Date of Patent: Jul. 13, 2010

(54) PYRROLIDINE DERIVATIVES ACTING AS CCR3-RECEPTOR ANTAGONISTS

(75) Inventors: Gurdip Bhalay, West Sussex (GB);
Andrew Dunstan, West Sussex (GB);
Angela Glen, Suffolk (GB); Trevor John Howe, Kraainem (BE); Clive McCarthy, Basel (CH)

(73) Assignee: Novartis AG, Basel (CH)

( * ) Notice: Subject to any disclaimer, the term of this patent is extended or adjusted under 35 U.S.C. 154(b) by 347 days.

(21) Appl. No.: 10/585,615

(22) PCT Filed: Jan. 28, 2005

(86) PCT No.: PCT/EP2005/000874

§ 371 (c)(1),
(2), (4) Date: Jun. 9, 2009

(87) PCT Pub. No.: WO2005/075420

PCT Pub. Date: Aug. 18, 2005

(65) Prior Publication Data

US 2009/0306138 A1 Dec. 10, 2009

(30) Foreign Application Priority Data

Jan. 30, 2004 (GB) ................... 0402101.0

(51) Int. Cl.
*C07D 207/12* (2006.01)
*A61K 31/40* (2006.01)
(52) U.S. Cl. .............. 514/424; 548/541; 548/556
(58) Field of Classification Search .......... 548/567
See application file for complete search history.

(56) References Cited

U.S. PATENT DOCUMENTS 5,274,097 A * 12/1993 Schohe et al. ............ 546/208
6,605,623 B1 * 8/2003 Ko et al. .................. 514/331

* cited by examiner

*Primary Examiner*—Rebecca L Anderson
*Assistant Examiner*—Matthew P Coughlin
(74) *Attorney, Agent, or Firm*—John Alexander

(57) ABSTRACT

Compounds of formula I

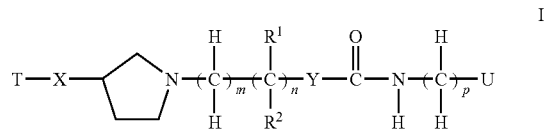

in free or salt form, wherein T, X, Y, U, $R^1$, $R^2$, m, n and p have the meanings as indicated in the specification, are useful for treating conditions mediated by CCR3. Pharmaceutical compositions that contain the compounds and processes for preparing the compounds are also described.

8 Claims, No Drawings

PYRROLIDINE DERIVATIVES ACTING AS CCR3-RECEPTOR ANTAGONISTS

This invention relates to organic compounds, their preparation and use as pharmaceuticals.

In one aspect, the invention provides compounds of formula I

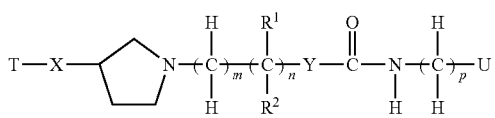

in free or salt form, wherein

T is phenyl or a 5- or 6-membered heterocyclic ring wherein at least one of the ring atoms is selected from the group consisting of nitrogen, oxygen and sulphur;

X is —O—, carbonyl or a bond;

$R^1$ and $R^2$ are independently selected from the group consisting of hydrogen, carboxy, $C_1$-$C_8$-alkoxy, and $C_1$-$C_8$-alkyl optionally substituted by hydroxy, $C_1$-$C_8$-alkoxy, acyloxy, halo, carboxy, $C_1$-$C_8$-alkoxycarbonyl, —N($R^a$)$R^b$, —CON($R^c$)$R^d$ or by a monovalent cyclic organic group having 3 to 15 atoms in the ring system;

Y is

where $R^3$ is hydrogen or $C_1$-$C_8$-alkyl, or Y is

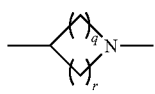

where q and r are independently 1 or 2;

U is a cyclic group selected from the group consisting of phenyl, $C_3$-$C_8$-cycloalkyl, and a 5- or 6-membered heterocyclic ring wherein at least one of the ring atoms is selected from the group consisting of nitrogen, oxygen and sulphur;

m is a whole number from 0 to 8;

n is an integer from 1 to 8 except when Y is

then n is an integer from 2 to 8;

p is a whole number from 0 to 4;

$R^a$- and $R^b$ are each independently hydrogen or $C_1$-$C_8$-alkyl, or $R^a$ is hydrogen and $R^b$ is hydroxy-$C_1$-$C_8$-alkyl, acyl, —$SO_2R^e$ or —CON($R^c$)$R^d$, or $R^a$ and $R^b$ together with the nitrogen atom to which they are attached denote a 5- or 6-membered heterocyclic group wherein at least one of the ring atoms is selected from the group consisting of nitrogen, oxygen and sulphur;

$R^c$ and $R^d$ are each independently hydrogen or $C_1$-$C_8$-alkyl, or $R^c$ and $R^d$ together with the nitrogen atom to which they are attached denote a 5- or 6-membered heterocyclic group wherein at least one of the ring atoms is selected from the group consisting of nitrogen, oxygen and sulphur; and $R^e$ is $C_1$-$C_8$-alkyl, $C_1$-$C_8$-haloalkyl, or phenyl optionally substituted by $C_1$-$C_8$-alkyl.

Terms used in the specification have the following meanings:

"Optionally substituted" means the group referred to can be substituted at one or more positions by any one or any combination of the radicals listed thereafter.

"Halo" or "halogen" as used herein denotes a element belonging to group 17 (formerly group VII) of the Periodic Table of Elements, which may be, for example, fluorine, chlorine, bromine or iodine. Preferably halo or halogen is fluorine or chlorine.

"$C_1$-$C_8$-alkyl" as used herein denotes straight chain or branched alkyl having 1 to 8 ring carbon atoms. Preferably $C_1$-$C_8$-alkyl is $C_1$-$C_4$-alkyl.

"$C_3$-$C_8$-cycloalkyl" denotes cycloalkyl having 3 to 8 ring carbon atoms, for example a monocyclic group such as a cyclopropyl, cyclobutyl, cyclopentyl, cyclohexyl, cycloheptyl or cyclooctyl, any of which can be substituted by one or more, usually one or two, $C_1$-$C_4$-alkyl groups, or a bicyclic group such as bicycloheptyl or bicyclooctyl. Preferably "$C_3$-$C_8$-cycloalkyl" is cyclopropyl, cyclobutyl, cyclopentyl, cyclohexyl, cycloheptyl or cyclooctyl.

"$C_1$-$C_8$-haloalkyl" as used herein denotes $C_1$-$C_8$-alkyl as hereinbefore defined substituted by one or more halogen atoms, preferably one, two or three halogen atoms.

"Acyl" as used herein denotes alkylcarbonyl, for example $C_1$-$C_8$-alkylcarbonyl where $C_1$-$C_8$-alkyl may be one of the $C_1$-$C_8$-alkyl groups hereinbefore mentioned, optionally substituted by one or more halogen atoms; cycloalkylcarbonyl, for example $C_3$-$C_8$-cycloalkylcarbonyl where $C_3$-$C_8$-cycloalkyl may be, for example, cyclopropyl, cyclobutyl, cyclopentyl, cyclohexyl, cycloheptyl or cyclooctyl; 5- or 6-membered heterocyclylcarbonyl having one or two hetero atoms selected from nitrogen, oxygen and sulfur in the ring, such as furylcarbonyl or pyridylcarbonyl; arylcarbonyl, for example $C_6$-$C_{10}$-arylcarbonyl such as benzoyl; or aralkylcarbonyl, for example $C_6$ to $C_{10}$-aryl-$C_1$-$C_4$-alkylcarbonyl such as benzylcarbonyl or phenylethylcarbonyl. Preferably acyl is $C_1$-$C_4$-alkylcarbonyl.

"$C_1$-$C_8$-alkoxy" as used herein denotes straight chain or branched alkoxy having 1 to 8 ring carbon atoms. Preferably $C_1$-$C_8$-alkoxy is $C_1$-$C_4$-alkoxy.

"$C_1$-$C_8$-alkoxycarbonyl" as used herein denotes $C_1$-$C_8$-alkoxy as hereinbefore defined attached through the oxygen atom to a carbonyl group.

"Acyloxy" as used herein denotes alkylcarbonyloxy, for example $C_1$-$C_8$-alkylcarbonyloxy where $C_1$-$C_8$-alkyl may be one of the $C_1$-$C_8$-alkyl groups hereinbefore mentioned, optionally substituted by one or more halogen atoms; cycloalkylcarbonyloxy, for example $C_3$-$C_8$-cyclo-alkylcarbonyloxy where $C_3$-$C_8$-cycloalkyl may be, for example, cyclopropyl, cyclobutyl, cyclopentyl, cyclohexyl, cycloheptyl or cyclooctyl; 5- or 6-membered heterocyclylcarbonyloxy having one or two hetero atoms selected from nitrogen, oxygen and sulfur in the ring, such as furylcarbonyloxy or pyridylcarbonyloxy; arylcarbonyloxy, for example $C_6$-$C_{10}$-aryl-carbonyloxy such as benzoyloxy; or aralkylcarbonyloxy, for example $C_6$ to $C_{10}$-aryl-$C_1$-$C_4$-alkylcarbonyloxy such as benzylcarbonyloxy or phenylethylcarbonyloxy, or aryloxyalkyl-carbonyloxy, for example, $C_6$-$C_{10}$-aryloxy-$C_1$-$C_8$-alkylcarbonyloxy, any of which is optionally substituted in the aryl moiety by at least one substituent selected from $C_1$-$C_8$-alkoxy, halogen, $C_1$-$C_8$-alkylcarbonyl, aminosulfonyl, $C_1$-$C_8$-alkylaminosulfonyl and di($C_1$-$C_8$-alkyl)aminosulfonyl. Preferably acyloxy is $C_1$-$C_4$-alkylcarbonyloxy, or benzoyloxy or phenoxy-$C_1$-$C_4$-alkylcarbonyloxy optionally substituted in the benzene ring thereof by at least one substituent selected from $C_1$-$C_4$-alkoxy, $C_1$-$C_4$-alkylcarbonyl or aminosulfonyl.

"5- or 6-membered heterocyclic ring containing at least one ring heteroatom selected from the group consisting of nitrogen, oxygen and sulphur" as used herein may be, for example, pyrrole, pyrrolidine, pyrazole, imidazole, triazole, tetrazole, thiadiazole, isothiazole, oxadiazole, pyridine, oxazole, isoxazole, pyrazine, pyridazine, pyrimidine, piperazine, morpholino, triazine, oxazine or thiazole.

The group denoted by T can be unsubstituted or substituted. Preferred substituents include halo, cyano, hydroxy, carboxy, nitro, amido, $C_1$-$C_8$-alkyl, and $C_1$-$C_8$-alkoxy optionally substituted by aminocarbonyl. T is preferably phenyl, which is preferably substituted by fluoro.

The cyclic group denoted by U can be unsubstituted or substituted. Preferred substituents include halo, cyano, hydroxy, carboxy, nitro, amido, $C_1$-$C_8$-alkyl, and $C_1$-$C_8$-alkoxy optionally substituted by aminocarbonyl or halo. The cyclic group denoted by U is preferably phenyl optionally substituted by halo (particularly fluoro and/or chloro), nitro or $C_1$-$C_8$-alkoxy.

Throughout this specification and in the claims that follow, unless the context requires otherwise, the word "comprise", or variations such as "comprises" or "comprising", will be understood to imply the inclusion of a stated integer or step or group of integers or steps but not the exclusion of any other integer or step or group of integers or steps.

Preferred compounds of formula I in free or salt form include those in which

T is phenyl optionally substituted by halo;

X is —O—;

$R^1$ and $R^2$ are both hydrogen;

Y is

where $R^3$ is hydrogen, or Y is

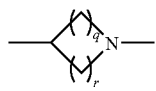

where q and r are both 2;

U is phenyl optionally substituted by halo, nitro or $C_1$-$C_8$-alkoxy;

m is a whole number from 0 to 8;

n is an integer from 1 to 8 except when Y is

then n is an integer from 2 to 8; and p is 0.

Especially preferred compounds of formula I in free or salt form include those in which T is phenyl optionally substituted by halo, preferably fluoro;

X is —O—;

$R^1$ and $R^2$ are both hydrogen;

Y is

where $R^3$ is hydrogen, or Y is

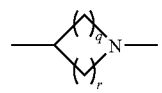

where q and r are both 2;

U is phenyl optionally substituted by halo, nitro or $C_1$-$C_4$-alkoxy, where halo is preferably fluoro and/or chloro;

m is a whole number from 0 to 4;

n is an integer from 1 to 4 except when Y is

then n is an integer from 2 to 4; and p is 0.

Many of the compounds represented by formula I are capable of forming acid addition salts, particularly pharmaceutically acceptable acid addition salts. Pharmaceutically acceptable acid addition salts of the compound of formula I include those of inorganic acids, for example, hydrohalic acids such as hydrofluoric acid, hydrochloric acid, hydrobromic acid or hydroiodic acid, nitric acid, sulfuric acid, phosphoric acid; and organic acids, for example aliphatic monocarboxylic acids such as formic acid, acetic acid, trifluoroacetic acid, prop-ionic acid and butyric acid, aliphatic hydroxy acids such as lactic acid, citric acid, tartaric acid or malic acid, dicarboxylic acids such as maleic acid or succinic acid, aromatic carboxylic acids such as benzoic acid, p-chlorobenzoic acid, diphenylacetic acid or triphenylacetic acid, aromatic hydroxy acids such as o-hydroxybenzoic acid, p-hydroxy-benzoic acid, 1-hydroxynaphthalene-2-carboxylic acid or 3-hydroxynaphthalene-2-carboxylic acid, and sulfonic acids such as methanesulfonic acid or benzenesulfonicacid. These salts may be prepared from compounds of formula I by known salt-forming procedures.

Compounds of formula I which contain acidic, e.g. carboxyl groups, are also capable of forming salts with bases, in particular pharmaceutically acceptable bases such as those well known in the art; suitable such salts include metal salts, particularly alkali metal or alkaline earth metal salts such as sodium, potassium, magnesium or calcium salts, or salts with ammonia or pharmaceutically acceptable organic amines or heterocyclic bases such as ethanolamines, benzylamines or pyridine. These salts may be prepared from compounds of formula I by known salt-forming procedures.

In those compounds where there is an asymmetric carbon atom the compounds exist in individual optically active isomeric forms or as mixtures thereof, e.g. as racemic or diastereomeric mixtures. The present invention embraces individual optically active R and S isomers as well as mixtures, e.g. racemic or diastereomeric mixtures, thereof.

Specific especially preferred compounds of the invention are those described hereinafter in the Examples.

The invention also provides a process for the preparation of compounds of formula I which comprises:

(i) reacting a compound of formula II

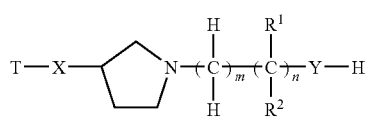

wherein T, X, $R^1$, $R^2$, Y, m and n are as hereinbefore defined, with a compound of formula III

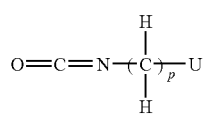

wherein p and U are as hereinbefore defined; and (ii) recovering the product in free or salt form.

This process may be carried out using known procedures for reacting amines with isocyanates, or analogously e.g. as hereinafter described in the Examples. The reaction is conveniently carried out using an organic solvent, for example dimethylformamide. Suitable reaction temperatures are from 10° C. to 40° C., for example room temperature.

Compounds of formula II are novel and may be prepared by reacting a compound of formula IV

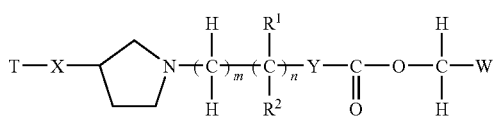

wherein T, X, $R^1$, $R^2$, Y, m and n are as hereinbefore defined and W denotes a solid phase substrate chemically linked to the indicated methylene group, with a reagent that cleaves the bond between the indicated —Y— and —$COOCH_2$—W, thereby detaching the compound of formula II from the substrate to replace —$COOCH_2$—W with hydrogen. The reaction may be effected using known methods for detaching substrate-bound amino compounds from a substrate, or analogously e.g. as hereinafter described in the Examples. The reaction is conveniently carried out under acidic conditions, for example using a mixture of trifluoroacetic acid (TFA) and an organic solvent such as dichloromethane (DCM). Suitable reaction temperatures are from 10° C. to 40° C., for example room temperature.

Compounds of formula III are either commercially available or may be obtained by known procedures for preparing isocyanates.

Compounds of formula IV may be prepared by reacting a compound of formula V

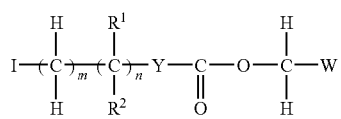

herein "Wang-Iodide resin" wherein $R^1$, $R^2$, Y, m, n and W are as hereinbefore defined, with a compound of formula VI

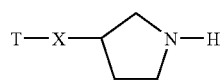

wherein T and X are as hereinbefore defined, using known procedures for reacting amino compounds with alkyl iodides, or analogously e.g. as hereinafter described in the Examples. The reaction is conveniently carried out in the presence of a non-nucleophilic acid scavenger such as diisopropylethylamine (DIPEA/Hünig's base) and using an organic solvent such as dimethylformamide (DMF). Suitable reaction temperatures are elevated temperatures, for example from 50° C. to 80° C., but preferably about 55° C.

Compounds of formula V may be prepared by reacting the corresponding primary alcohol of formula VII

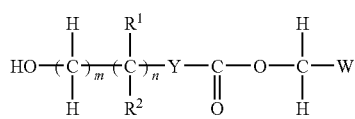

wherein $R^1$, $R^2$, Y, m, n and W are as hereinbefore defined, with iodine, for example using known procedures such as reaction in an inert organic solvent such as a mixture of tetrahydrofuran (THF) and acetonitrile in the presence of a triarylphosphine and a base such as imidazole, conveniently at a temperature are from 10° C. to 40° C., for example room temperature.

Compounds of formula VI are either commercially available or may be prepared using known methods.

Compounds of formula VII may be prepared by reacting a compound of formula VIII

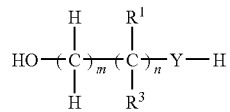

wherein $R^1$, $R^2$, Y, m and n are as hereinbefore defined, with a compound of formula IX

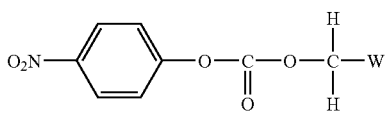

wherein W is a solid phase substrate, the resin-based compound of formula IX being hereinafter referred to as "Wang para-nitrophenol resin" or "Wang-PNP resin", or analogously e.g. as hereinafter described in the Examples. The reaction is conveniently carried out using an organic solvent such as dimethylformamide (DMF). Suitable reaction temperatures are from 10° C. to 40° C., but preferably room temperature.

Compounds of formula VIII are either commercially available or may be prepared using known methods.

Compounds of formula IX can be prepared by reacting p-nitrophenyl chloroformate with a compound of formula X

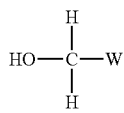

using known procedures for reacting haloformates with alcohols, or analogously e.g. as hereinafter described in the Examples. The reaction is conveniently carried out in the presence of an organic base, for example N-methylmorpholine, and using an organic solvent such as dichloromethane (DCM). Suitable reaction temperatures are from 10° C. to 40° C., but preferably room temperature.

Resin-based compounds of formula X are commercially available, for example as modified polystyrene resins such as Wang resin having a p-hydroxymethyl-substituted phenoxyalkyl attached to skeletal benzene rings of the polystyrene.

Compounds of formula I in free form may be converted into salt form, and vice versa, in a conventional manner. The compounds in free or salt form can be obtained in the form of hydrates or solvates containing a solvent used for crystallisation. Compounds of formula I can be recovered from reaction mixtures and purified in a conventional manner. Isomers, such as enantiomers, may be obtained in a conventional manner, e.g. by fractional crystallisation or asymmetric synthesis from correspondingly asymmetrically substituted, e.g. optically active, starting materials.

Compounds of formula I in free or pharmaceutically acceptable salt form, hereinafter referred to alternatively as agents of the invention, are useful as pharmaceuticals. Accordingly the invention also provides a compound of formula I in free or pharmaceutically acceptable salt form for use as a pharmaceutical. The agents of the invention act as CCR-3 receptor antagonists, thereby inhibiting the infiltration and activation of inflammatory cells, particularly eosinophils, and inhibiting allergic response. The inhibitory properties of agents of the invention can be demonstrated in the following assay:

Recombinant cells expressing human CCR-3 are captured by wheatgerm agglutinin (WGA) polyvinyltoluidene (PVT) SPA beads (available from Amersham), through a specific interaction between the WGA and carbohydrate residues of glycoproteins on the surface of the cells. [$^{125}$I]-human eotaxin (available from Amersham) binds specifically to CCR-3 receptors bringing the [$^{125}$I]-human eotaxin in close proximity to the SPA beads. Emitted â-particles from the [$^{125}$I]-human eotaxin excite, by its proximity, the fluorophore in the beads and produce light. Free [$^{125}$I]-human eotaxin in solution is not in close proximity to the scintillant and hence does not produce light. The scintillation count is therefore a measure of the extent to which the test compound inhibits binding of the eotaxin to the CCR-3.

Preparation of Assay Buffer: 5.96 g HEPES and 7.0 g sodium chloride are dissolved in distilled water and 1 M aqueous $CaCl_2$ (1 ml) and 1M aqueous $MgCl_2$ (5 ml) are added. The pH is adjusted to 7.6 with NaOH and the solution made to a final volume of 1 l using distilled water. 5 g bovine serum albumin and 0.1 g sodium azide are then dissolved in the solution and the resulting buffer stored at 4° C. A COMPLETE™protease inhibitor cocktail tablet (available from Boehringer) is added per 50 ml of the buffer on the day of use.

Preparation of Homogenisation Buffer: Tris-base (2.42 g) is dissolved in distilled water, the pH of the solution is adjusted to 7.6 with hydrochloric acid and the solution is diluted with distilled water to a final volume of 1 l. The resulting buffer is stored at 4° C. A COMPLETE™protease inhibitor cocktail tablet is added per 50 ml of the buffer on the day of use.

Preparation of membranes: Confluent rat basophil leukaemia (RBL-2H3) cells stably expressing CCR3 are removed from tissue culture flasks using enzyme-free cell dissociation buffer and resuspended in phosphate-buffered saline. The cells are centrifuged (800 g, 5 minutes), the pellet resuspended in ice-cold homogenisation buffer using 1 ml homogenisation buffer per gram of cells and incubated on ice for 30 minutes. The cells are homogenised on ice with 10 strokes in a glass mortar and pestle. The homogenate is centrifuged (800 g, 5 minutes, 4° C.), the supernatant further centrifuged (48,000 g, 30 minutes, 4° C.) and the pellet redissolved in Homogenisation Buffer containing 10% (v/v) glycerol. The protein content of the membrane preparation is estimated by the method of Bradford (*Anal. Biochem.* (1976) 72:248) and aliquots are snap frozen and stored at −80° C. The assay is performed in a final volume of 250 μl per well of an OPTIPLATE™ microplate (ex Canberra Packard). To selected wells of the microplate are added 50 μl of solutions of a test compound in Assay Buffer containing 5% DMSO (concentrations from 0.01 nM to 10 μM). To determine total binding, 50 μl of the Assay Buffer containing 5% DMSO is added to other selected wells. To determine non-specific binding, 50 μl of 100 nM human eotaxin (ex R&D Systems) in Assay Buffer containing 5% DMSO is added to further selected wells. To all wells are added 50 μl [$^{125}$I]-Human eotaxin (ex Amersham) in Assay Buffer containing 5% DMSO at a concentration of 250 pM (to give a final concentration of 50 pM per well), 50 μL of WGA-PVT SPA beads in Assay Buffer (to give a final concentration of 1.0 mg beads per well) and 100 μl of the membrane preparation at a concentration of 100 μg protein in Assay Buffer (to give a final concentration of 10 μg protein per well). The plate is then incubated for 4 hours at room temperature. The plate is sealed using TOPSEAL-S™ (ex Canberra Packard) according to the manufacturer's instructions. The resulting scintillations are counted using a Canberra Packard TopCount, each well being counted for 1 minute. The concentration of test compound at which 50% inhibition occurs ($IC_{50}$) is determined from concentration-inhibition curves in a conventional manner.

The compounds of the Examples hereinbelow have $IC_{50}$ values of the order of 1.6 μM or less in the above assay. For instance, the compounds of Examples 2 and 3 have $IC_{50}$ values of 0.270 and 0.446 µM respectively.

Having regard to their inhibition of binding of CCR-3, agents of the invention are useful in the treatment of conditions mediated by CCR-3, particularly inflammatory or allergic conditions. Treatment in accordance with the invention may be symptomatic or prophylactic.

Accordingly, agents of the invention are useful in the treatment of inflammatory or obstructive airways diseases, resulting, for example, in reduction of tissue damage, bronchial hyperreactivity, remodelling or disease progression. Inflammatory or obstructive airways diseases to which the present invention is applicable include asthma of whatever type or genesis including both intrinsic (non-allergic) asthma and extrinsic (allergic) asthma, mild asthma, moderate asthma, severe asthma, bronchitic asthma, exercise-induced asthma, occupational asthma and asthma induced following bacterial infection. Treatment of asthma is also to be understood as embracing treatment of subjects, e.g. of less than 4 or 5 years of age, exhibiting wheezing symptoms and diagnosed or diagnosable as "wheezy infants", an established patient category of major medical concern and now often identified as incipient or early-phase asthmatics. (For convenience this particular asthmatic condition is referred to as "wheezy-infant syndrome".)

Prophylactic efficacy in the treatment of asthma will be evidenced by reduced frequency or severity of symptomatic attack, e.g. of acute asthmatic or bronchoconstrictor attack, improvement in lung function or improved airways hyperreactivity. It may further be evidenced by reduced requirement for other, symptomatic therapy, i.e. therapy for or intended to restrict or abort symptomatic attack when it occurs, for example antiinflammatory (e.g. corticosteroid) or bronchodilatory. Prophylactic benefit in asthma may in particular be apparent in subjects prone to "morning dipping". "Morning dipping" is a recognised asthmatic syndrome, common to a substantial percentage of asthmatics and characterised by asthma attack, e.g. between about 4 to 6 am, i.e. at a time normally substantially distant form any previously administered symptomatic asthma therapy.

Other inflammatory or obstructive airways diseases and conditions to which the present invention is applicable include acute lung injury (ALI), acute/adult respiratory distress syndrome (ARDS), chronic obstructive pulmonary, airways or lung disease (COPD, COAD or COLD), including chronic bronchitis or dyspnea associated therewith, emphysema, as well as exacerbation of airways hyperreactivity consequent to other drug therapy, in particular other inhaled drug therapy. The invention is also applicable to the treatment of bronchitis of whatever type or genesis including, e.g., acute, arachidic, catarrhal, croupus, chronic or phthinoid bronchitis. Further inflammatory or obstructive airways diseases to which the present invention is applicable include pneumoconiosis (an inflammatory, commonly occupational, disease of the lungs, frequently accompanied by airways obstruction, whether chronic or acute, and occasioned by repeated inhalation of dusts) of whatever type or genesis, including, for example, aluminosis, anthracosis, asbestosis, chalicosis, ptilosis, siderosis, silicosis, tabacosis and byssinosis.

Having regard to their anti-inflammatory-activity, in particular in relation to inhibition of eosinophil activation, agents of the invention are also useful in the treatment of eosinophil related disorders, e.g. eosinophilia, in particular eosinophil related disorders of the airways (e.g. involving morbid eosinophilic infiltration of pulmonary tissues) including hypereosinophilia as it effects the airways and/or lungs as well as, for example, eosinophil-related disorders of the airways consequential or concomitant to Löffler's syndrome, eosinophilic pneumonia, parasitic (in particular metazoan) infestation (including tropical eosinophilia), bronchopulmonary aspergillosis, polyarteritis nodosa (including Churg-Strauss syndrome), eosinophilic granuloma and eosinophil-related disorders affecting the airways occasioned by drug-reaction.

Agents of the invention are also useful in the treatment of inflammatory or allergic conditions of the skin, for example psoriasis, contact dermatitis, atopic dermatitis, alopecia areata, erythema multiforma, dermatitis herpetiformis, scleroderma, vitiligo, hypersensitivity angiitis, urticaria, bullous pemphigoid, lupus erythematosus, pemphisus, epidermolysis bullosa acquisita, and other inflammatory or allergic conditions of the skin.

Agents of the invention may also be used for the treatment of other diseases or conditions, in particular diseases or conditions having an inflammatory component, for example, treatment of diseases and conditions of the eye such as conjunctivitis, keratoconjunctivitis sicca, and vernal conjunctivitis, diseases affecting the nose including allergic rhinitis, and inflammatory conditions of the gastrointestinal tract, for example inflammatory bowel disease such as ulcerative colitis and Crohn's disease.

The effectiveness of an agent of the invention in inhibiting inflammatory conditions, for example in inflammatory, airways diseases, may be demonstrated in an animal model, e.g. a mouse or rat model, of airways inflammation or other inflammatory conditions, for example as described by Szarka et al, *J. Immunol. Methods* (1997) 202:49-57; Renzi et al, *Am. Rev. Respir. Dis.* (1993) 148:932-939; Tsuyuki et al., *J. Clin. Invest.* (1995) 96:2924-2931; and Cernadas et al (1999) *Am. J. Respir. Cell Mol. Biol.* 20:1-8.

The agents of the invention are also useful as co-therapeutic agents for use in combination with other drug substances such as anti-inflammatory, bronchodilatory, antihistamine, decongestant or anti-tussive drug substances, particularly in the treatment of obstructive or inflammatory airways diseases such as those mentioned hereinbefore, for example as potentiators of therapeutic activity of such drugs or as a means of reducing required dosaging or potential side effects of such drugs. An agent of the invention may be mixed with the other drug substance in a fixed pharmaceutical composition or it may be administered separately, before, simultaneously with or after the other drug substance. Suitable anti-inflammatory drugs include steroids, in particular glucocorticosteroids such as budesonide, beclamethasone dipropionate, fluticasone propionate, ciclesonide or mometasone furoate, or steroids described in WO 02/88167, WO 02/12266, WO 02/100879, WO 02/00679 (especially those of Examples 3, 11, 14, 17, 19, 26, 34, 37, 39, 51, 60, 67, 72, 73, 90, 99 and 101), WO 03/35668, WO 03/48181, WO 03/62259, WO 03/64445, WO 03/72592, WO 04/39827 and WO 04/66920; non-steroidal glucocorticoid receptor agonists, such as those described in DE 10261874, WO 00/00531, WO 02/10143, WO 03/82280, WO 03/82787, WO 03/86294, WO 03/104195, WO 03/101932, WO 04/05229, WO 04/18429, WO 04/19935 and WO 04/26248; LTD4 antagonists such as montelukast and zafirlukast; PDE4 inhibitors such cilomilast (Ariflo® GlaxoSmithKline), Roflumilast (Byk Gulden), V-11294A (Napp), BAY19-8004 (Bayer), SCH-351591 (Schering-Plough), Arofylline (Almirall Prodesfarma), PD189659/PD168787 (Parke-Davis), AWD-12-281 (Asta Medica), CDC-801 (Celgene), SelCID™ CC-10004 (Celgene), VM554/UM565 (Vernalis), T-440 (Tanabe), KW-4490 (Kyowa Hakko Kogyo), and those disclosed in WO 92/19594, WO 93/19749, WO 93/19750, WO 93/19751, WO 98/18796, WO 99/16766, WO 01/13953, WO 03/104204, WO 03/104205, WO 03/39544, WO 04/000814, WO 04/000839, WO 04/005258, WO 04/018450, WO 04/018451, WO 04/018457, WO 04/018465, WO 04/018431, WO 04/018449, WO 04/018450, WO 04/018451, WO 04/018457, WO 04/018465, WO 04/019944, WO 04/019945, WO 04/045607 and WO 04/037805; $A_{2A}$ agonists such as those described in EP 1052264, EP 1241176, EP 409595A2, WO 94/17090, WO 96/02543, WO 96/02553, WO 98/28319, WO 99/24449, WO 99/24450, WO 99/24451, WO 99/38877, WO 99/41267, WO 99/67263, WO 99/67264, WO 99/67265, WO 99/67266, WO 00/23457, WO 00/77018, WO 00/78774, WO 01/23399, WO 01/27130, WO 01/27131, WO 01/60835, WO 01/94368, WO 02/00676, WO 02/22630, WO 02/96462, and WO 03/086408; and $A_{2B}$ antagonists such as those described in WO 02/42298.

Suitable bronchodilatory drugs include anticholinergic or antimuscarinic agents, in particular ipratropium bromide, oxitropium bromide, tiotropium salts and CHF 4226 (Chiesi), and glycopyrrolate, but also those described in EP 424021, U.S. Pat. No. 3,714,357, U.S. Pat. No. 5,171,744, WO 01/04118, WO 02/00652, WO 02/51841, WO 02/53564, WO 03/00840, WO 03/33495, WO 03/53966, WO 03/87094, WO 04/018422 and WO 04/05285; and beta-2 adrenoceptor agonists such as albuterol (salbutamol), metaproterenol, terbutaline, salmeterol fenoterol, procaterol, and especially, formoterol, carmoterol and pharmaceutically acceptable salts thereof, and compounds (in free or salt or solvate form) of formula I of WO 0075114, which document is incorporated herein by reference, preferably compounds of the Examples thereof, especially a compound of formula

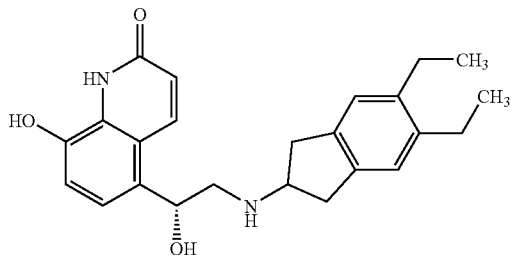

and pharmaceutically acceptable salts thereof, as well as compounds (in free or salt or solvate form) of formula I of WO 04/16601, and also compounds of EP 1440966, JP 05025045, WO 93/18007, WO 99/64035, US 2002/0055651, WO 01/42193, WO 01/83462, WO 02/66422, WO 02/70490, WO 02/76933, WO 03/24439, WO 03/42160, WO 03/42164, WO 03/72539, WO 03/91204, WO 03/99764, WO 04/16578, WO 04/22547, WO 04/32921, WO 04/33412, WO 04/37768, WO 04/37773, WO 04/37807, WO 04/39762, WO 04/39766, WO 04/45618 WO 04/46083 and WO 04/80964.

Suitable dual anti-inflammatory and bronchodilatory drugs include dual beta-2 adrenoceptor agonist/muscarinic antagonists such as those disclosed in US 2004/0167167, WO 04/74246, WO 04/74812 and US 2004/0242622.

Suitable antihistamine drug substances include cetirizine hydrochloride, acetaminophen, clemastine fumarate, promethazine, loratidine, desloratidine, diphenhydramine and fexofenadine hydrochloride, activastine, astemizole, azelastine, ebastine, epinastine, mizolastine and tefenadine as well as those disclosed in JP 2004107299, WO 03/099807 and WO 04/026841.

Combinations of agents of the invention and steroids, beta-2 agonists, PDE4 inhibitors or LTD4 antagonists may be used, for example, in the treatment of COPD or, particularly, asthma. Combinations of agents of the invention and anticholinergic or antimuscarinic agents, PDE4 inhibitors, dopamine receptor agonists or LTB4 antagonists may be used, for example, in the treatment of asthma or, particularly, COPD.

Other useful combinations of agents of the invention with anti-inflammatory drugs are those with other antagonists of chemokine receptors, e.g. CCR-1, CCR-2, CCR-3, CCR-4, CCR-5, CCR-6, CCR-7, CCR-8, CCR-9 and CCR10, CXCR1, CXCR2, CXCR3, CXCR4, CXCR5, particularly CCR-5 antagonists such as Schering-Plough antagonists SC-351125, SCH-55700 and SCH-D, Takeda antagonists such as N-[[4-[[[6,7-dihydro-2-(4-methylphenyl)-5H-benzocyclohepten-8-yl]carbonyl]amino]phenyl]-methyl]tetrahydro-N,N-dimethyl-2H-pyran-4-amin-ium chloride (TAK-770), and CCR-5 antagonists described in U.S. Pat. No. 6,166,037 (particularly claims 18 and 19), WO 00/66558 (particularly claim 8), WO 00/66559 (particularly claim 9), WO 04/018425 and WO 04/026873.

In accordance with the foregoing, the invention also provides a method for the treatment of a condition mediated by CCR-3, for example an inflammatory or allergic condition, particularly an inflammatory or obstructive airways disease, which comprises administering to a subject, particularly a human subject, in need thereof an effective amount of a compound of formula I in a free or pharmaceutically acceptable salt form as hereinbefore described. In another aspect the invention provides the use of a compound of formula I, in free or pharmaceutically acceptable salt form, as hereinbefore described for the manufacture of a medicament for the treatment of a condition mediated by CCR-3, for example an inflammatory or allergic condition, particularly an inflammatory or obstructive airways disease.

The agents of the invention may be administered by any appropriate route, e.g. orally, for example in the form of a tablet or capsule; parenterally, for example intravenously; by inhalation, for example in the treatment of inflammatory or obstructive airways disease; intranasally, for example in the treatment of allergic rhinitis; topically to the skin, for example in the treatment of atopic dermatitis; or rectally, for example in the treatment of inflammatory bowel disease.

In a further aspect, the invention also provides a pharmaceutical composition comprising as active ingredient a compound of formula I in free or pharmaceutically acceptable salt form, optionally together with a pharmaceutically acceptable diluent or carrier therefor. The composition may contain a co-therapeutic agent such as an anti-inflammatory or bronchodilatory drug as hereinbefore described. Such compositions may be prepared using conventional diluents or excipients and techniques known in the galenic art. Thus oral dosage forms may include tablets and capsules. Formulations for topical administration may take the form of creams, ointments, gels or transdermal delivery systems, e.g. patches. Compositions for inhalation may comprise aerosol or other atomizable or dry powder formulations.

When the composition comprises an aerosol formulation, it preferably contains, for example, a hydro-fluoro-alkane (HFA) propellant such as HFA134a or HFA227 or a mixture of these, and may contain one or more co-solvents known in the art such as ethanol (up to 20% by weight), and/or one or more surfactants such as oleic acid or sorbitan trioleate, and/ or one or more bulking agents such as lactose. When the composition comprises a dry powder formulation, it preferably contains, for example, the compound of formula I having a particle diameter up to 10 microns, optionally together with a diluent or carrier, such as lactose, of the desired particle size distribution and a compound that helps to protect against product performance deterioration due to moisture, e.g. magnesium stearate. When the composition comprises a nebulised formulation, it preferably contains, for example, the compound of formula I either dissolved, or suspended, in a vehicle containing water, a co-solvent such as ethanol or propylene glycol and a stabiliser, which may be a surfactant.

The invention includes (A) an agent of the invention in inhalable form, e.g. in an aerosol or other atomizable composition or in inhalable particulate, e.g. micronised form, (B) an inhalable medicament comprising an agent of the invention in inhalable form; (C) a pharmaceutical product comprising such an agent of the invention in inhalable form in association with an inhalation device; and (D) an inhalation device containing an agent of the invention in inhalable form.

Dosages of agents of the invention employed in practising the present invention will of course vary depending, for example, on the particular condition to be treated, the effect desired and the mode of administration. In general, suitable daily dosages for administration by inhalation are of the order of 0.01 to 30 mg/kg while for oral administration suitable daily doses are of the order of 0.01 to 100 mg/kg.

The invention is illustrated by the following Examples.

EXAMPLES

Especially preferred compounds of formula I are also compounds of formula XI

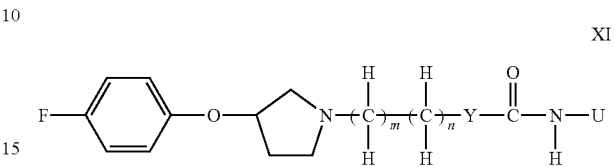

wherein m, n, Y and U are as shown in the following table, their methods of preparation being described hereinafter. The table also shows characterising mass spectrometry data ([MH]+). All compounds are in the free form.

TABLE I

| Ex. | m | n | Y | U | MS [MH]+ |
|---|---|---|---|---|---|
| 1 | 0 | 1 | (4-piperidinyl-N—) | (3-methoxyphenyl) | — |
| 2 | 1 | 2 | —NH— | (3-methoxyphenyl) | 388.1 |
| 3 | 1 | 2 | —NH— | (3,4-difluorophenyl) | 394.1 |
| 4 | 1 | 2 | —NH— | (3-methoxy-4-chlorophenyl) | 422.1 |
| 5 | 1 | 3 | —NH— | (phenyl) | 372.2 |
| 6 | 1 | 3 | —NH— | (4-methoxy-2-nitrophenyl) | 447.1 |

Preparation of Starting Materials

Wang-PNP Resin

4-Nitrophenylchloroformate (260 g, 1.30 mmol) as a solution in 500 ml dichloromethane (DCM) is added to Wang resin (p-benzyloxybenzyl alcohol resin ex Calbiochem-Nova-biochem, 350 g, 0.60 mmol) suspended in 1000 ml DCM and N-methylmorpholine (196 ml, 1.79 mmol) and stirred at room temperature for 18 hours. The resin is filtered and washed successively using methanol, DCM and ether to give WANG PARA-NITROPHENOL RESIN. [IR. 1761.5 cm$^{-1}$; Loading 1.20 mmol/g].

Wang-Iodide Resin 27 ml of 350 mmol 1-amino-3-propanol is added to a suspension of 93 g, 116.4 mmol WANG-PNP RESIN in dimethylformamide (DMF) and stirred at room temperature for 18 hours. The mixture is filtered and the resin washed in succession with methanol, DCM and finally ether to give the Wang-amino propanol resin (Wang-AP resin). To this a mixture of tetrahydrofuran (THF) and methyl cyanide (1000 ml, 1:1 v/v) is added, followed by triphenylphosphine (91.8 g, 350 mmol), iodine (88.83 g, 350 mmol) and imidazole (23.83 g, 350 mmol). The suspension is stirred at room temperature for 24 hours, filtered and then washed with copious DMF, DCM and methanol to give WANG-IODIDE RESIN.

3-Hydroxy-pyrrolidine-1-carboxylic acid tert-butyl ester

Di-tert-butyl-dicarbonate (764 g, 350 mmol) as a solution in 1,4-dioxane (100 ml) is added to 3-hydroxy-pyrrolidine 1 (23.43 g, 269 mmol) in a mixture of water/1,4-dioxane (350 ml, 1:1 v/v) and sodium hydrogen carbonate (68 g, 807 mmol) and the mixture stirred at room temperature for 18 hours. After which the organic layer is separated, dried (using MgSO$_4$), filtered and evaporated to give the title compound as a thick colourless oil.

3-Methanesulphonyloxy-pyrrolidine-1-carboxylic acid tert-butyl ester

3-Hydroxy-pyrrolidine-1-carboxylic acid tert-butyl ester is dissolved in dry pyridine (20 ml) and cooled to −5° C. Methanesulphonyl chloride is added over a period of 10 minutes keeping the temperature between −5° C. and 0° C. after which the yellow solution is allowed to warm up to room temperature over a period of 30 minutes. Water (20 ml) is added and the mixture is then extracted using DCM (2×30 ml), the organic washings being combined and washed with 2N potassium hydrogen sulphate solution (2×30 ml). The organic phase is dried (using MgSO$_4$), filtered and evaporated to give the title compound as a colourless oil.

3-(4-fluoro-phenoxy)-pyrrolidine-1-carboxylic acid tert-butyl ester

Sodium hydride (554 mg, 13.84 mmol) is added to a solution of 4-fluorophenol (1.60 g, 14.20 mmol) in DMF (20 ml) and the mixture is stirred at room temperature for 2 minutes. 3-Methanesulphonyloxy-pyrrolidine-1-carboxylic acid tert-butyl ester is added and the mixture heated at 60° C. for 18 hours. Water (50 ml) is then added and the resulting product is extracted using diethyl ether (3×30 ml). The organic extracts are dried (using MgSO$_4$), filtered and evaporated to give a white solid, which is purified using column chromatography over silica gel (ethyl acetate/isohexane 1:9 v/v) to give the title compound.

3-(4-Fluoro-phenoxy)-pyrrolidine 4N hydrogen chloride in dioxane (200 ml) is added to a solution of 3-(4-fluoro-phenoxy)-pyrrolidine-1-carboxylic acid tert-butyl ester 5 (39.43 g, 140 mmol) in ethanol (200 ml) and the mixture stirred at room temperature for 18 hours. The solvent is evaporated under vacuum and the residue basified using 4N sodium hydroxide solution (200 ml). The resulting product is extracted using DCM (3×100 ml). The organic extracts are dried (using MgSO$_4$), filtered and evaporated to give the title compound as a light brown oil.

Example 1

4-[3-(4-fluoro-phenoxy)-pyrrolidine-1-yl-methyl]-piperidine-1-carboxylic acid (3-methoxy-phenyl)-amide 2.6 ml of 14.73 mmol diisopropylethylamine and 2.67 g of 14.73 mmol 3-(4-Fluoro-phenoxy)-pyrrolidine are added to a suspension of WANG-IODIDE RESIN (5.8 g, 7.37 mmol) in DMF (100 ml) and the mixture stirred at 55° C. for 60 hours. The resin is cooled and washed using DMF (8×40 ml), methanol (2×50 ml) and DCM (12×40 ml). The washed resin is treated with a mixture of trifluoroacetic acid (TFA)/DCM (50 ml, 1:1 v/v) for 40 minutes at room temperature, filtered and the filtrate evaporated. The residue is treated with basic resin (AMBERLYST™ A-21) to give to give Resin Intermediate I of formula II.

1-Isocyanato-3-methoxy-benzene (19 mg, 0.126 mmol) in DMF (2 ml) is added to a solution of Resin Intermediate I (50 mg, 0.180 mmol) in DMF (2 ml) and the mixture left to stand for 1 hour at room temperature. Polymer-bound isocyanate is added to the mixture to remove excess primary amine. The solution is then dispensed on to a strong cation exchange (SCX) eluting using 1M ammonia in methanol to give the title compound as a white solid.

Example 2

1-{3-[3-(4-fluorophenoxy)pyrrolidine-1-yl]propyl}-3-(3-methoxyphenyl)-urea 2.6 ml of 14.73 mmol diisopropylethylamine (DIPEA) and 3-(4-fluorophenoxy)-pyrrolidine is mixed with a suspension of 5.8 g, 7.37 mmol WANG-IODIDE RESIN in 100 ml DMF and stirred at 55° C. for 60 hours. The resin is cooled and washed using DMF (8×40 ml), methanol (2×50 ml) and DCM (12×40 ml). The resin is then treated with a mixture of TFA and DCM (50 ml, 1:1 v/v) at room temperature for 40 minutes, filtered and the filtrate evaporated. The residue is treated with the basic resin (AMBERLYST™ A-21) to give Resin Intermediate II of formula II.

3-Methoxyphenyl isocyanate (188 mg 1.25 mmol) in 5 ml dimethylformamide (DMF) is added to a solution of Resin Intermediate II (300 mg, 1.25 mmol) in 10 ml DMF and the mixture is left to stand at room temperature for 1 hour. The solvent is evaporated and the residue purified by chromatography to yield the title product as a white solid [MH+ 388.1].

Examples 3 to 6

The compounds of Examples 3 to 6, are prepared using procedures analogous to those used in Example 2, using appropriate starting materials.

The invention claimed is:

1. A compound of formula I

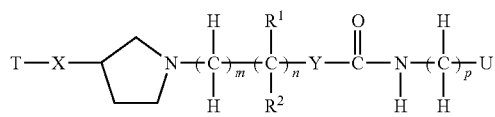

in free or pharmaceutically acceptable salt form, wherein

T is phenyl or a 5- or 6-membered heterocyclic ring wherein at least one of the ring atoms is selected from the group consisting of nitrogen, oxygen and sulphur;

X is —O—, carbonyl or a bond;

$R^1$ and $R^2$ are independently selected from the group consisting of hydrogen, carboxy, $C_1$-$C_8$-alkoxy, and $C_1$-$C_8$-alkyl optionally substituted by hydroxy, $C_1$-$C_8$-alkoxy, acyloxy, halo, carboxy, $C_1$-$C_8$-alkoxycarbonyl, —N($R^a$)$R^b$, —CON($R^c$)$R^d$ or by a monovalent cyclic organic group having 3 to 15 atoms in the ring system;

Y is

where $R^3$ is hydrogen or $C_1$-$C_8$-alkyl,

U is a cyclic group selected from the group consisting of phenyl, $C_3$-$C_8$-cycloalkyl, and a 5- or 6-membered heterocyclic ring wherein at least one of the ring atoms is selected from the group consisting of nitrogen, oxygen and sulphur;

m is a whole number from 0 to 8;

n is an integer from 1 to 8 except when Y is

then n is an integer from 2 to 8;

p is a whole number from 0 to 4;

$R^a$ and $R^b$ are each independently hydrogen or $C_1$-$C_8$-alkyl, or $R^a$ is hydrogen and $R^b$ is hydroxy-$C_1$-$C_8$-alkyl, acyl, —$SO_2R^e$ or —CON($R^c$)$R^d$, or $R^a$ and $R^b$ together with the nitrogen atom to which they are attached denote a 5- or 6-membered heterocyclic group wherein at least one of the ring atoms is selected from the group consisting of nitrogen, oxygen and sulphur;

$R^c$ and $R^d$ are each independently hydrogen or $C_1$-$C_8$-alkyl, or $R^c$ and $R^d$ together with the nitrogen atom to which they are attached denote a 5- or 6-membered heterocyclic group wherein at least one of the ring atoms is selected from the group consisting of nitrogen, oxygen and sulphur; and $R^e$ is $C_1$-$C_8$-alkyl, $C_1$-$C_8$-haloalkyl, or phenyl optionally substituted by $C_1$-$C_8$-alkyl.

2. A compound according to claim 1, wherein

T is phenyl optionally substituted by halo;

X is —O—;

$R^1$ and $R^2$ are both hydrogen;

Y is

where $R^3$ is hydrogen,

U is phenyl optionally substituted by halo, nitro or $C_1$-$C_8$-alkoxy;

m is a whole number from 0 to 8;

n is an integer from 1 to 8 except when Y is

then n is an integer from 2 to 8; and p is 0.

3. A compound according to claim 1, wherein

T is phenyl optionally substituted by halo, preferably fluoro;

X is —O—;

$R^1$ and $R^2$ are both hydrogen;

Y is

where $R^3$ is hydrogen,

U is phenyl optionally substituted by halo, nitro or $C_1$-$C_4$-alkoxy, where halo is preferably fluoro and/or chloro;

m is a whole number from 0 to 4;

n is an integer from 1 to 4 except when Y is

then n is an integer from 2 to 4; and p is 0.

4. A compound according to claim 1 that is also a compound of formula XI

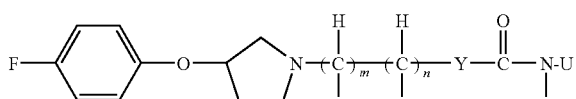

in free or pharmaceutically acceptable salt form, wherein m, n, Y and U are as shown in the following table:

| m | n | Y | U |
|---|---|---|---|
| 1 | 2 | —NH— | 3-methoxyphenyl |
| 1 | 2 | —NH— | 3,4-difluorophenyl |
| 1 | 2 | —NH— | 4-chloro-2-methoxyphenyl (H3CO, Cl) |
| 1 | 3 | —NH— | phenyl |
| 1 | 3 | —NH— | 4-methoxy-2-nitrophenyl (OCH3, O⁻—N⁺=O) |

5. A compound according to claim 1 for use as a pharmaceutical.

6. A compound according to claim 1 in combination with at least one drug substance which is an anti-inflammatory, a bronchodilator, an antihistamine, a decongestant or an antitussive drug substance.

7. A pharmaceutical composition comprising as an active ingredient a compound according to claim 1, optionally together with a pharmaceutically acceptable diluent or carrier therefor.

8. A process for the preparation of a compound of formula I in free or pharmaceutically acceptable salt form as defined in claim 1, which comprises:

(i) reacting a compound of formula II

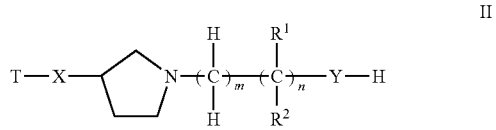

II wherein T, X, $R^1$, $R^2$, Y, m and n are as defined in claim 1, with a compound of formula III

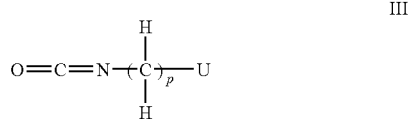

III wherein p and U are as defined in claim 1; and (ii) recovering the product in free or pharmaceutically acceptable salt form.

* * * * *